United States Patent [19]

Akutin et al.

[11] 4,146,739

[45] Mar. 27, 1979

[54] PROCESS FOR PRODUCING PHENOL-FORMALDEHYDE OLIGOMERS OF ORTHO-SPECIFIC STRUCTURE

[76] Inventors: Modest S. Akutin, B. Tishinsky pereulok, 26, korpus 16, kv. 16, Moscow; Alexandr N. Ustkachkintsev, ulitsa Kozlova, 11, kv. 29, Orekhovo-Zuevo Moskovskoi oblasti; Boris V. Yakobson, ulitsa garety "Pravda", 11, kv. 35, Orekhovo-Zuevo Moskovskoi oblasti; Boris A. Potapov, ulitsa Lopatina, 4, kv. 8, Orekhovo-Zuevo Moskovskoi oblasti; Irina I. Zhuravleva, prospekt Kirova, 58a, kv.11, Kuibyshev; Galina B. Kopteva, ulitsa Dekabristov, 164, kv. 46, Kazan, all of U.S.S.R.

[21] Appl. No.: 748,713

[22] Filed: Dec. 8, 1976

[51] Int. Cl.² .................. C07C 37/00; C07C 37/20
[52] U.S. Cl. ................................................ 568/720
[58] Field of Search .................... 260/619 A; 568/720

[56] References Cited
U.S. PATENT DOCUMENTS

| | | | |
|---|---|---|---|
| 2,744,882 | 5/1956 | Bender et al. | 260/619 A |
| 2,754,335 | 7/1956 | Bender et al. | 260/619 A |
| 3,330,873 | 7/1967 | Godin et al. | 260/619 A |

*Primary Examiner*—Norman Morgenstern
*Attorney, Agent, or Firm*—Lackenbach, Lilling & Siegel

[57] ABSTRACT

The process for producing phenol-formaldehyde oligomers of ortho-specific structure comprises reacting finely-divided crystalline phenol or a mixture of crystalline phenol with crystalline naphthalene, containing from 14 to 58 wt.% of the latter, at a temperature of from 20° to 40° C. with gaseous formaldehyde to give phenolic alcohols. The thus-prepared phenolic alcohols are subjected to polycondensation simultaneously with drying and subsequent heat-treatment of the resulting oligomers of ortho-specific structure.

The process according to the present invention makes it possible to intensify the production of phenol-formaldehyde oligomers of ortho-specific structure. Furthermore, owing to the fact that this process makes it possible to eliminate the use of catalysts and high temperatures, it simplifies technology of the production of phenol-formaldehyde oligomers.

The resulting oligomers (in the case of using mixtures of phenol with naphthalene for the production of phenolic alcohols) are more heat-resistant.

5 Claims, No Drawings

PROCESS FOR PRODUCING PHENOL-FORMALDEHYDE OLIGOMERS OF ORTHO-SPECIFIC STRUCTURE

The present invention relates to processes for producing phenol-formaldehyde oligomers of ortho-specific structure.

The invention is useful in the production of a binder for compositions possessing stable working properties.

Articles produced from such compositions are suitable for operation under conditions of elevated temperatures, high pressures and ionizing irradiation.

Known in the art are processes for the production of phenol-formaldehyde oligomers — ortho-novolacs which comprise conventional polycondensation of the starting components, i.e. phenol and formaldehyde, in a melt or solution in the presence of salts of bivalent metals or organic acids.

In solutions, the process is first conducted at reflux until at least 30% of formaldehyde is combined and the molar ratio between phenol and formaldehyde is reduced to 1:1.1. The second reaction stage is conducted under milder conditions at a temperature within the range of from 100° to 120° C. for a longer period ensuring the formation of 20–25% of methylol groups by weight of the resin or at a temperature of from 150° to 160° C. under pressure with recycle of the condensate into the reaction zone.

In a melt, o-novolac is obtained in the presence of a concentrated hydrochloric acid or a 1% solution of $Zn(CH_3COO)_2 \cdot 2H_2O$ at a molar ratio of phenol to $CH_2O$ of from 1:2.5 to 1:3. The process is performed in 4 stages: reaction of addition (formation of methylphenols) $CH_2O$ (to 75–90%), distilling-off water, condensation (of phenol with methylphenols) at 130° C. and distilling-off excessive amounts of phenol under vacuum.

Also known in the art is a gas-liquid polycondensation process for the production of ortho-novolac oligomers possessing high thermoreactivity in a mixture with hexamethylene tetramine based on a so-called phenol-formaldehyde master-batch and without making use of a catalyst. The latter was prepared (cf. German (Federal Republic) Pat. No. 849,485 1952) by saturation of a molten synthetic phenol or other kinds of phenolic stock with formaldehyde contained in contact gases of formalin production. Unlike phenol which solidifies at a temperature of 40° C. and formalin, said phenol-formaldehyde master-batch may be stored and transported without pre-heating — this constitutes its advantage. However, due to high humidity of the contact gases being used it has been heretofore impossible to obtain such phenol-formaldehyde master-batch with a water content below 15 wt.% (pH=5–6 at the ratio of phenol to formaldehyde of 100:30) and 4.5% of methanol content, whereby the phenol-formaldehyde polycondensation rate is substantially reduced and additional drying of the resulting resin is required. In order to produce oligomers of ortho-specific structure and to further intensify the process, the condensation is conducted in two stages: first, under pressure at a temperature of from 130° to 170° C.; then, the resulting initial condensation products are added with an acidic catalyst and the reaction is continued under atmospheric pressure at the boiling temperature.

A process has been also described, wherein as the starting materials use is made of a mixture of phenol with paraform. Adding this mixture to the phenol-formaldehyde master-batch without, however, introducing catalysts, oligomers are obtained with a gelatinization rate much the same as that of o-novolacs prepared in the presence of ortho-orientation catalysts. This technique, nevertheless, has not provided a reduced water-content in the final resins.

Naphthalene-formaldehyde resins have been first prepared (cf. U.S. Pat. No. 2,330,827) by reacting phenol with the products of naphthalene-aldehyde condensation. Said naphthalene-aldehyde condensation as well as subsequent reaction of phenol with the condensation products are preferably conducted in the presence of acidic catalysts (sulphuric or phosphoric acid). Naphthalene is used in the form of a pure solid substance or in the form of compressed tablets produced by filtration of a coal resin distilled within the range of from 130° to 250° C.; in some cases use is made of a coal resin as it is. Formaldehyde takes part in the condensation in the form of an aqueous solution with a concentration of from 32 to 52%. For this reason, into the starting mixture there have been introduced in advance 20–25% of water and 20% of foreign impurities, whereby the propagation rate of a molecular chain is considerably reduced, the water-content and, hence, energy consumption is substantially increased.

Recently a process has been developed for the production of such oligomers by a single-stage method involving co-condensation of eutectic mixtures of aromatic hydrocarbons with any reactivity and polycyclicity with phenol and formaldehyde in a slightly-acidic medium at a temperature within the range of from 80° to 110° C. Federal Republic of Germany Pat. No. 2,014,175. This process is superior over the previously known two-stage process in the fact that it does not require the use of special acid-resistant equipment and regeneration of substantial amounts of sulphuric acid (amount of the catalyst employed does not exceed 1% by weight of the resin). As the starting raw materials use is made of waste products of coal-tar chemical industry, whereby the production costs of the final products are substantially reduced. However, this process still has some disadvantages and, first of all, the most serious disadvantage resides in the use of high temperatures and catalysts.

It is an object of the present invention to eliminate the above-mentioned disadvantages.

It is the main object of the present invention to provide a process wherein wherein the production of phenol-formaldehyde oligomers of ortho-specific structure could be effected by means of a simplified technology.

It is another object of the present invention to provide a process wherein it is possible to intensify the production of phenol-formaldehyde oligomers with ortho-specific structure.

Still another object of the present invention is to provide a process which would enable increased heat-resistance of the resulting phenol-formaldehyde oligomers of ortho-specific structure.

The process according to the present invention resides in producing phenol-formaldehyde oligomers of ortho-specific structure by reacting a phenol-containing compound with gaseous formaldehyde, followed by condensation of the resulting primary products, drying and heat-treating the obtained oligomers. In accordance with the present invention, the phenol-containing compound can be finely-divided phenol or of a mixture of crystalline phenol with crystalline naphthalene, containing from 14 to 58 wt.% of naphthalene, and the process of the formation of the primary products, i.e. phenolic alcohols, is conducted at a temperature within the range of from 20° to 40° C.

The present invention has made it possible to intensify the process for the preparation of phenol-formaldehyde oligomers of ortho-specific structure due to the fact that the first stage of the process, i.e. production of phenolic alcohols, is conducted in an anhydrous medium at the interface between a solid substance (crystal) and gas using as the starting reagents gaseous formaldehyde and crystalline phenol or its mixture with crystalline naphthalene.

The use, according to the invention, of crystalline phenol in the process of our invention makes it possible to substantially accelerate the formation of phenolic alcohols and eliminate the use of of a catalyst. Therewith, a temperature is maintained at which phenol is not molten and, hence, the molecules retain their specific orientation relative to each other.

Naphthalene, entering in the mixture, does not react with phenol during polycondensation but forms molecular complexes therewith of the donor-acceptor type which are rather durable. Presence of these complexes in the mixture activates it and makes it still more reactive as compared to pure phenol. It provides an opportunity to conduct the process at room temperature using only water-cooling (since the process is exothermal by its nature). The process is economically efficient, since it is effected without using a catalyst.

Furthermore, the use of similar reagents makes it possible to considerably reduce the amount of gas liquor and, hence, to lower energy consumption for the production; this facilitates the preparation of rapidly-curing modified phenol-formaldehyde oligomers of orthospecific structure featuring an increased heat-resistance and mechanical strength retained at elevated temperatures. Therefore, the process according to the present invention has the following advantages enabling:

a) minimized steam consumption rate for the reactor heating;

b) elimination of drying of the oligomer being produced due to the absence of gas liquor, since the amount of gas liquor at the output of 30,000 t/year is reduced from 21,000 t/year down to 2,000 t/year;

c) substantial decrease of energy consumption for combustion of the resulting gas liquor.

These advantages make it possible to reduce production costs of the final product by 10–13%, while the initial investments are reduced by 30 to 50%.

To increase the desired product yield, it is advisable, in accordance with the present invention, that the process of producing primary products, i.e. phenolic alcohols, be conducted at a temperature within the range of from 20° to 25° C.

To increase the degree of conversion of the crystalline reagent and to accelerate the process of producing phenol-formaldehyde oligomers, the phenolic alcohols are continuously removed from the reaction zone when the process per se is performed continuously as well.

Further objects and advantages of the present invention will now become more fully apparent from the following detailed description.

The synthesis of ortho-specific oligomers of the novolac type involves, quite conditionally, 5 stages: reaction of addition of gaseous formaldehyde to the crystalline phenol-containing compound (production of the primary products of polycondensation); condensation; drying (removal of the polycondensation water); heat-treatment and distilling-off the excessive amount of phenol under vacuum.

Production of the primary products of polycondensation is performed in a reactor of a batch or continuous action. A periodic-action reactor comprises a cylindrical apparatus provided with a magnetic stirrer, bubbling means, thermometer and a water-cooling jacket.

As the starting reagents use is made of a crystalline phenol-containing compound and gaseous formaldehyde which is obtained by the method of thermal destruction from paraform (or α-polyoxymethylene) pre-dried at a temperature of 60° C. and residual pressure of 60 mm Hg to a maximum water content of 0.006 wt.%. The suspension composition charged into the formaldehyde generator is as follows: 37 parts by weight of paraform and 63 parts by weight of ditolylmethane (B.p. about 400° C.) serving as a heat-transfer medium. All the communication lines supplying the resulting gas from a generator to the reactor are heated to the temperature of 130° C. thus preventing formation of paraform upon cooling of the gas and clogging of the pipelines.

The polycondensation process according to the present invention imposes strict requirements on the starting monomers, primarily on their reactivity. Failure to meet this requirement might result in dissolution of the gaseous monomer in the reaction products with the formation of an anhydrous solution which, in this case, constitutes the reaction zone of the process. The use of finely divided crystalline phenol or a mixture of crystalline phenol with crystalline naphthalene as the starting reagent makes it possible to substantially intensify the process of producing phenolic alcohols and obviates the necessity of introducing a catalyst in the process. It has been experimentally established that best results are obtained when using mixtures of crystalline phenol with crystalline naphthalene, containing from 14 to 58 wt.% of the latter.

The temperature is maintained below the melting point of phenol, thus preventing phenol molecules from becoming disoriented with respect to each other, i.e. the temperature is equal to 20°–40° C. Kinetic studies have shown maximum conversion degree to be attained at a temperature of 20°–25° C. and pH of the medium of from 6.3 to 6.8. Chromatographic analysis of the reaction mixture has also shown that phenolic alcohols are mainly produced therewith which contain ortho-bonds (of the saligenine type) and oligomers based thereon are obtained at the highest yield and with higher physico-mechanical properties.

The essence of the process of the present invention resides in that gaseous formaldehyde is first admitted into a reactor and passed through a bed of finely-divided crystalline phenol with a particle size of about 150μ. The unreacted gas is entrapped in an absorption flask by an aqueous solution of $Na_2SO_3$ with the formation of NaOH thus making it possible to evaluate the amount of unreacted gas leaving the reactor. During the entire test period, water at a temperature of 15° to 18° C. is continuously passed through the reactor jacket. The whole system is preliminary purged with argon, since the presence of air oxygen even in minor amounts results, in the presence of residual humidity contained in the gas, in oxidation of formaldehyde to formic acid. The latter, while in vaporous state, is entrained by the gas and passed into the reactor thus substantially decreasing the medium pH down to 4.5–5.3. In such cases the amount of o-o'-isomers is considerably lowered and regularity of the final product structure is impaired (i.e. gelatinization time of novolacs becomes substantially (increased).

In the very beginning, the periodic process proceeds in a two-phase system at the interface between the crystalline substance and gas (1 stage). As the reaction progresses, in the reaction medium a third phase is formed, i.e. liquid phenolic alcohols (II stage). This stage should be regarded as transitional; it is characterized by unstable hydrodynamic conditions due to susceptibility of the crystalline phenol-containing compound to aggregation in a liquid phase. As a result of accumulation of a particular amount of phenolic alcohols they progressively dissolve all the unreacted phenol. Therewith, the whole system again becomes two-phased but, at this time, it is a gas-liquid system (III stage), whereby the rate of formation of phenolic alcohols is substantially reduced. Meanwhile, adsorption of gas in the system is sharply increased. Therefore, chemical reaction of addition is progressively displaced by a purely physical process of saturation of the medium with gaseous formaldehyde. The content of free formaldehyde in the medium will determine which resins either of novolac or resol-type will be obtained. Maximal conversion degree of phenol (26%) corresponds to t = 25° C. and, in contrast to other conditions, is achieved for a shorter period of time. Chromatographic analysis of the reaction mixture has shown that in the first stage of the polycondensation process only phenolic alcohols are produced which contain mainly ortho-bonds.

In the continuous process for the production of primary polycondensation products, the phenol-containing component is continuously fed into a column-type apparatus and uniformly distributed on a plate. Gaseous formaldehyde is fed through a bubbling means located in the bottom section of the column. Reaction conditions are the same as in the periodic process, except that in this case the resulting products (phenolic alcohols) are continuously discharged from the reactor, wherefore it becomes possible to achieve a higher conversion degree of the crystalline component (50 to 60 wt.%).

The faster phenolic alcohols are removed from the reaction zone, the smaller will be phenol losses and the higher will be its conversion (the desired product yield).

Condensation of oligomers and removal of the polycondensation liquid (gas liquor) is effected in a reactor provided with a stirrer, Dean-Stark trap with a reflux condenser for collecting distillate and a thermometer. The process is performed at a temperature within the range of from 130° to 165° C. The amount of resulting gas liquor was not more than 7% by weight.

On completion of condensation and drying, the excess phenol is removed from the mixture with the novolac oligomer under vacuum at a final temperature of 150° C. and residual pressure of 60 mm Hg with simultaneous heat-treatment effected for the purpose of maximal increase of deformational heat-resistance and dropping point of the oligomers.

EXAMPLE 1

Finely-divided crystalline phenol in the amount of 20 g (0.21 mole) is charged into a four-neck cylindrical reactor provided with an outlet pipe for the removal of an excessive amount of gas, a thermometer, stirrer, bubbling means and a cooling jacket. Gaseous formaldehyde is fed from a generator, with paraform, at a temperature of 130° C. into the reactor, wherein the gas is bubbled through a bed of fine-divided crystalline phenol. Chromatographic analysis has shown that during the first 10 minutes the formation reaction of orthophenolic alcohols occurs. The reaction medium temperature is 25±3° C.; pH = 6.3–6.5. Condensation is conducted at a temperature of 130° C. for 40 minutes constantly increasing, afterwards, the temperature to 165° C. whereupon the oligomer drying is effected. The amount of gas liquor is not more than 5% by weight. Heat-treatment of the novolac phenol-formaldehyde oligomer is performed at a temperature of 150° C. and residual pressure of 60 mm Hg for a period of from 15 to 30 minutes.

Gelatinization time (curing on the electric stove at a temperature of 150° C. with 14 parts by weight of urotropin) is 30 to 40 sec.; molecular weight is 630; ubbelohde drop point — 94° C.; bromizing agent content (free residual phenol) — 5%; starting temperature of intensive destruction — 385° C.; Ostwald viscosity of a 50% solution in ethanol — 110 cps; yield — 65%; o-o'-isomers content — 49.4%.

EXAMPLE 2

Phenolic alcohols are produced in a cylindrical apparatus with an outlet pipe intended for evacuation of an excess amount of gas. Crystalline finely-divided phenol in the amount of 20 g (0.21 mole) is continuously fed into the reactor and uniformly distributed over a metallic screen (plate) with a hole diameter of 0.1 mm. Gaseous formaldehyde is fed into the reactor through a bubbling means located under the metallic screen. The reaction medium temperature is 23°–25° C.; pH is 6.3–6.8. As the phenolic acids are formed, they are continuously discharged from the apparatus. It is advisable to use vacuum for this purpose. The subsequent stages are performed in much the same manner as in the foregoing Example 1.

Gelatinization time (curing of the oligomer at 150° C. with 14 parts by weight of urotropin) is 35–50 sec; molecular weight is 600; Ubbelohde drop point is 90° C.; viscosity of a 50% solution in ethanol, according to Ostwald — 100 cps; starting temperature of intensive destruction — 385° C.; yield — 68%; bromizing agent content — 6%; o-o'-isomers content — 51%.

EXAMPLE 3

Finely-divided crystalline phenol in the amount of 20 g (0.21 mole) is charged into a batch reactor. The reaction medium temperature is 36±3° C.; pH = 6.6. During first 12 minutes phenolic alcohols are produced. Total duration of contact between the two phases is 20 minutes. At a longer period of passing the gas through the reaction mixture a resol-type oligomer is produced. Further stages of the process are performed in a manner similar to that described in the foregoing Example 1.

Gelatinization time (curing on an electric stove at 150° C. with 14 parts by weight of urotropin) is 40–60 sec; molecular weight is 480; Ubbelohde drop point is 90° C.; Ostwald viscosity of a 50% solution in ethanol is 100 cps; starting temperature of intensive destruction is 360° C.; yield — 57%; amount of gas liquor 5–7%; o-o'-isomer content 44%; bromizing agent content — 6%.

EXAMPLE 4

25 g of finely-divided crystalline mixture consisting of 86 wt% of phenol and 14 wt.% of naphthalene (i.e.

the phenol-to-naphthalene molar ratio being 8.38:1) are charged into a batch reactor.

Oligomer is prepared in a manner similar to that described in Example 1.

The reaction medium temperature is maintained at 23°±3° C.; pH = 6.5. Time of contacting the two phases is 18 min. Gelatinization time (curing on an electric stove at the temperature of 150° C. with 14 wt.% of urotropin) is 20-28 sec; molecular weight of the final product is 830; Ubbelohde drop point is 102° C.; Ostwald viscosity of a 50% solution in ethanol is 105 cps; starting point of intensive destruction is 390° C.; oligomer yield is 67%; gas liquor content is 6%.

EXAMPLE 5

A finely-divided crystalline eutectic mixture of phenol with naphthalene in the amount of 25 g is charged into a batch reactor. Oligomer is prepared in a manner similar to that described in the foregoing Example 1. The reaction medium temperature in the synthesis of the primary condensation products is maintained at 23°±3° C.; pH = 6.5. Optimal time required for contacting the two phases (crystal-gas) is 18 minutes.

Gelatinization time (curing on an electric stove at a temperature of 150° C. with 14 parts by weight of urotropin) is 12-20 sec; molecular weight of the final product is 1,230; Ubbelohde drop point is 108° C.; Ostwald viscosity of a 50% solution in ethanol is 100 cps; starting point of intensive destruction is 425° C.; oligomer yield — 65%; amount of gas liquor — 7%; o-p'-isomer content is 71%.

EXAMPLE 6

A crystalline finely-divided eutectic mixture of phenol and naphthalene in the amount of 10 g is continuously charged into a continuous-type reactor. The process is performed in much the same as in the foregoing Example 2. The reaction medium temperature is maintained at 23°-25° C.; pH = 6.8.

Gelatinization time (curing on an electric stove at the temperature of 150° C. with 14 parts by weight of urotropin) is 20-32 sec; molecular weight is 1,200; Ubbelohde drop point is 102° C.; Ostwald viscosity of a 50% solution in ethanol — 100 cps; starting point of intensive destruction 400° C.: oligomer yield — 70%; o-p'-isomer content — 70%.

EXAMPLE 7

25 g of a finely-divided crystalline mixture consisting of 80 wt.% of phenol and 20 wt.% of naphthalene (i.e. with the phenol-to-naphthalene ratio being 5.4:1) are charged into a batch reactor. Oligomer is prepared in the same manner as described in Example 1. The reaction medium temperature is maintained at 23°±3° C.; pH = 6.7. Time of contacting two phases is 20 min.

Gelatinization time (curing on an electric store at a temperature of 150° C. with 14 wt.% of urotropin) is 12-25 sec; molecular weight of the final product is 1230; Ubbelohde drop point is 105° C.; Ostwald viscosity of a 50% solution in ethanol is 95 cps; starting temperature of intensive destruction is 420° C.; oligomer yield is 65%; gas liquor content is 7%.

EXAMPLE 8

A finely-divided crystalline mixture of phenol with naphthalene in the amount of 20 g (with the composition being 58 wt.% of naphthalene per 42 wt.% of phenol or mole per mole) is charged into a batch reactor. The oligomer is produced in the same manner as described in Examples 1 and 4. Temperature of the reaction medium is maintained at 25° C.; pH is 6.3-6.5. Optimal time for contacting two phases is 16 minutes.

Gelatinization time (curing on an electric stove at a temperture of 150° C. with urotropin) is 12-25 sec; molecular weight is 1,260; Ubbelohde drop point is 100° C.; Ostwald viscosity of a 50% solution in ethanol is 100 cps; starting temperature of intensive destruction is 415° C.; oligomer yield is 72%; o-p'-isomer content is 65%.

What is claimed is:

1. In a process for the production of phenol-formaldehyde oligomers of ortho-specific structure comprising
   (1) reacting formaldehyde with a phenol compound to give phenolic alcohols;
   (2) polycondensation of said phenolic alcohols and simultaneous drying of the resulting phenol-formaldehyde oligomers at a temperature of 130°-165° C.; and
   (3) subjecting said oligomers to heat-treatment in a vacuum, the improvement comprising in the first step, reacting under anhydrous conditions and in the absence of oxygen, gaseous formaldehyde with finely-divided crystalline phenol or a mixture of crystalling phenol and naphthalene at a temperature ranging from 20°-40° C., to produce phenolic alcohols of ortho-specific structure.

2. A process for producing phenol-formaldehyde oligomers of ortho-specific structure as claimed in claim 1, wherein the formation of phenolic alcohols is conducted at a temperature ranging from 20° to 25° C.

3. A process for producing phenol-formaldehyde oligomers of ortho-specific structure as claimed in claim 1, wherein in the continuous production of said oligomers the phenolic alcohols are continuously removed from the reaction zone.

4. The process of claim 1, wherein said gaseous formaldehyde is obtained from the thermal destruction of pre-dried paraform.

5. The process of claim 1, wherein the phenol-formaldehyde oligomers are heat treated at 150° C. and a vacuum pressure of 60 mm Hg.

* * * * *